US010495619B2

(12) United States Patent
Thar et al.

(10) Patent No.: US 10,495,619 B2
(45) Date of Patent: Dec. 3, 2019

(54) DEVICE FOR DETERMINING A CONCENTRATION OF AN ANALYTE IN A GASEOUS MEDIUM

(71) Applicant: Pyro Science GmbH, Aachen (DE)

(72) Inventors: Roland Thar, Aachen (DE); Jan Fischer, Aachen (DE)

(73) Assignee: Pyro Science GmbH, Aachen (DE)

( * ) Notice: Subject to any disclaimer, the term of this patent is extended or adjusted under 35 U.S.C. 154(b) by 242 days.

(21) Appl. No.: 15/675,300

(22) Filed: Aug. 11, 2017

(65) Prior Publication Data

US 2018/0045699 A1 Feb. 15, 2018

(30) Foreign Application Priority Data

Aug. 11, 2016 (DE) .......................... 10 2016 114 918

(51) Int. Cl.
*G01N 33/00* (2006.01)
*G01N 21/63* (2006.01)

(52) U.S. Cl.
CPC ......... *G01N 33/0027* (2013.01); *G01N 21/63* (2013.01)

(58) Field of Classification Search
CPC ........ G01N 21/62; G01N 21/63; G01N 21/64; G01N 21/783; G01N 2021/7786; G01N 33/0004; G01N 33/0009; G01N 33/0027
USPC .............................................. 73/31.04, 31.05
See application file for complete search history.

(56) References Cited

U.S. PATENT DOCUMENTS

| | | | |
|---|---|---|---|
| 5,865,942 A | 2/1999 | Sinclair | |
| 2007/0212792 A1* | 9/2007 | Havens | ................. G01M 3/226 436/172 |
| 2008/0247906 A1* | 10/2008 | Heffels | ................ G01N 21/643 422/52 |
| 2013/0145845 A1 | 6/2013 | Enquist | |

FOREIGN PATENT DOCUMENTS

| | | |
|---|---|---|
| DE | 102014112972 A1 | 3/2015 |
| JP | 2008107091 | 5/2008 |
| WO | WO02061399 A1 | 8/2002 |
| WO | WO2005/100957 A1 | 10/2005 |
| WO | WO2013/181679 A1 | 12/2013 |
| WO | WO2015143229 A1 | 9/2015 |

* cited by examiner

*Primary Examiner* — Benjamin R Schmitt
(74) *Attorney, Agent, or Firm* — Von Rohrscheidt Patents

(57) ABSTRACT

A device for determining at least one condition parameter relating to a concentration or a partial pressure of an analyte in a gaseous medium, the device including at least one light source configured to emit light; at least one light receiver configured to detect the light; at least one optical sensor unit, and at least one temperature measuring device configured to measure a temperature of the optical sensor unit at least indirectly, wherein at least the light source, the light receiver and the temperature measuring device are arranged within a housing and at least the sensor unit is arranged outside of the housing, wherein at least one optical property of the sensor unit is a function of the condition parameter of the analyte, wherein light rays emitted by the sensor unit due to the sensor unit being irradiated by the light source are detectable by the light receiver.

14 Claims, 2 Drawing Sheets

DEVICE FOR DETERMINING A CONCENTRATION OF AN ANALYTE IN A GASEOUS MEDIUM

RELATED APPLICATIONS

This application claims priority from German Patent Application DE 10 2016 114 918.7 filed on Aug. 11, 2016 which is incorporated in its entirety by this reference.

FIELD OF THE INVENTION

A device for determining at least one condition parameter, in particular a concentration and/or a partial pressure of an analyte, in particular oxygen, in a gaseous medium, in particular an air volume flow.

BACKGROUND OF THE INVENTION

Devices of the generic type described supra are known in the art. The devices are used for example for determining a concentration of oxygen in a gaseous volume flow. A typical application can be for example determining an oxygen concentration in air that is exhaled by a person in order to determine how much oxygen has to be added to the exhaled air so that the exhaled air is suitable for the person as fresh breathing air.

The sensor units of these devices are typically made from a luminescent chemical substance whose luminescence changes as a function of the concentration of the analyte. An excitation of the sensor unit with light causes a light radiation from the sensor unit, wherein properties of the radiation coming from the sensor unit allow a conclusion with respect to the concentration of the analyte in or at the sensor unit.

Various devices are known in the art which use this technology or a comparable technology for determining a concentration of an analyte in a media flow. Reference is made to the International patent applications WO 2005/100957 A1 and WO 2013/181679 A1 and German Patent Application DE 10 2014 112 972 A1.

A typical problem when determining a concentration of an analyte with an optical sensor unit is that this type of sensor unit has a very high sensitivity relative to changing temperatures. This sensitivity has the effect that luminescent properties of the sensor unit also change as a function of the temperature change. Therefore it is not possible to derive a direct conclusion from a change of the luminescence of the sensor unit with respect to the cause of the change so that in particular no direct conclusion regarding the concentration of the analyte in the medium to be analyzed is possible.

In order to deal with the problem temperature sensors are used in the art which continuously monitor the temperature of the sensor unit. Thus, it is particularly relevant that a change of the temperature of the sensor unit is detected rather quickly so that it can be considered when processing the radiation emitted by the sensor unit. In case there is a time lag between the change of the temperature of the sensor unit and its detection by a temperature measuring device initially a particular transition time has to be provided when the temperature of the sensor unit changes before a reliable statement regarding the concentration of the respectively analyzed analyte can be made. Furthermore it is relevant that the temperature of the sensor unit deviates as little as possible from the temperature that is detected by the temperature measuring device. Deviations can be introduced by different temperatures of the medium to be examined and the housing. These deviations can have a negative influence upon the precision of the measurement of the analyte.

In order to keep the described time lag and temperature differences at a minimum it is proposed in the art for example to bring a temperature measuring device in direct contact with the respective sensor unit and to detect a temperature change of the sensor unit with the smallest delay possible. This method, however, has the problem that the respective temperature measuring device has to be run out of the electronics housing of the device and is therefore in direct contact with the respective medium to be analyzed like the sensor unit. In particular, there is a risk that an unintentional passage of the medium to be analyzed occurs through the opening of the housing into the housing wherein the opening is provided for the temperature measuring device so that the electronics are damaged.

BRIEF SUMMARY OF THE INVENTION

Thus, it is object of the invention to provide a device which facilitates a reliable determination of the concentration of the respective analyte that is being analyzed in the respective medium and which overcomes the configuration disadvantages of known devices.

The object is achieved by the device according to the invention improving upon the device recited supra by a thermal insulation layer which is configured to at least thermally separate the optical sensor unit from the medium that is to be examined. The separation shall be provided at least in that the temperature variations of the media flow are only transferred to the sensor unit with a large delay and advantageously not at all. Furthermore the insulation layer shall minimize potential temperature differences between the temperature measuring device in an interior of the housing and the sensor unit outside of the housing, advantageously avoid them completely.

The object is achieved in particular by a device for determining at least one condition parameter, in particular a concentration and/or a partial pressure of an analyte, in particular oxygen, in a gaseous medium, in particular an air volume flow, the device including at least one light source configured to emit light, at least one light receiver configured to detect light, at least one optical sensor unit, and at least one temperature measuring device configured to measure a temperature of the sensor unit at least indirectly, wherein at least the light source, the light receiver and the temperature measuring device are arranged within a housing and at least the sensor unit is arranged outside of the housing, wherein at least one optical property of the sensor unit is a function of the condition parameter of the analyte, wherein light rays emitted by the sensor unit due to the sensor unit being irradiated by the light source are detectable by the light receiver, wherein data captured this way by the light receiver facilitate a conclusion regarding the condition parameter of the analyte in the medium.

A light source according to the invention is a device that is configured to emit light. This light does not necessarily have to be light that is visible to the human eye. Instead the light can for example be infrared radiation or ultra violet radiation, in particular a LED can be the light source.

A light receiver according to the instant application is a device that is configured to transform a received light radiation into particular information. In particular it is conceivable that a light receiver of this type is configured to transform the received light into an electrical voltage or an electrical current. In any case it has to be possible that the light receiver provides the capability to receive information through the light that reaches the light receiver.

A light receiver of this type can be configured in particular for light that is not processed by the human eye, in particular infrared radiation. For example the light receiver can be formed by a photo diode.

An optical sensor unit according to the instant application is a sensor unit which facilitates a conclusion with respect to an analyzed analyte by putting out optical information. According to the instant application these are in particular sensor units whose optical properties change as a function of respective condition parameters, for example a concentration of the respective analyte.

A typical example for a sensor unit of this type is a sensor unit that has luminescent properties wherein the luminescence of the sensor unit changes as a function of a concentration of the respective analyte. Consequently an excitation of a sensor unit of this type by the light source and the light subsequently emitted by the sensor unit can facilitate a conclusion which concentration of the analyte is provided in the analyzed gaseous medium.

As an alternative to luminescent sensor units also absorbing sensor units and all other technically feasible sensor units are conceivable.

An absorbing sensor unit absorbs a different amount of light as a function of the condition parameter so that a conclusion with respect to the condition parameter of the analyte can be drawn from the analysis of a non-absorbed portion. A housing according to the instant application is a defined space in which typically at least all electronic components of the device are arranged.

The housing can be configured open or closed wherein the latter can be useful in particular when humidity penetration into the housing and thus an associated damage to electronic components of the device are at risk. An open configuration can provide in particular an advantage through pressure balancing between the components of the device and the ambient.

The housing can include in particular a divider wall which provides a direct spatial separation between a media space and an interior space of the housing wherein the medium and the sensor unit are arranged on a side of the media space and the remaining components of the device are arranged on a side of the interior space. In particular a divider wall, possibly the entire housing can be formed from a transparent material, so that a passage of light through the divider wall is facilitated. A thermal insulation layer according to the instant application is a layer whose primary purpose is to provide a thermal insulation of the sensor unit from the medium to be analyzed. In so far a thermal insulation layer is defined by its ability to provide this thermal insulation. Differently therefrom insulation layers that are known in the art which shall provide an optical insulation of the respective sensor unit are not equivalent to the thermal insulation layer according to the instant application since the known insulation layers are not suited as thermal insulation layers since they can hardly prevent a transfer of thermal energy from one side of the respective layer to another side or cannot prevent the transfer at all.

It is appreciated that each layer has a particular heat capacity which enables the layer to absorb a particular amount of thermal energy. Advantageously the thermal insulation layer according to the invention is configured so that it has a heat capacity of at least 0.3 J/gK, advantageously at least 0.5 J/gK, further advantageously 0.8 J/gK. An insulation layer of this type is particularly well suited to transfer a temperature of the analyzed medium to the sensor unit, since the insulation layer itself changes its temperature rather slowly.

It is appreciated that the thermal insulation layer has to cooperate with the remaining device so that a direct passage of the media volume flow is prevented at the optical sensor unit, so that at least no substantial direct exchange of thermal energy, for example due to convection, is possible between the medium and the sensor unit. In case the direct exchange were still provided in spite of the thermal insulation layer, the thermal insulation layer would be ineffective. Consequently it is appreciated that the insulation layer has to be permeable at least in some way for the respective analyte to be examined so that in spite of shielding the media flow from the optical sensor unit at least a migration of individual particles of the analyte is facilitated from the medium to the optical sensor unit. Thus, it is particularly advantageous when the thermal insulation layer is configured porous, in particular open porous. As a matter of principle also a diffusion of an analyte is possible through a solid material. A porous configuration of the insulation layer is advantageous for obtaining a minimum heat transfer coefficient of the insulation layer.

The device according to the invention has many advantages. In particular it is assured by using the thermal insulation layer that a change of the temperature of the respectively analyzed medium if transmitted at all is transmitted to the sensor unit only with a substantial delay. A sudden change of the temperature of the sensor unit that is always a risk in the prior art is thus prevented. Furthermore short term temperature spikes of the analyzed medium are almost or ideally completely without any impact upon the temperature of the sensor unit. Should a long term change of the temperature of the medium occur it is appreciated that also the temperature of the sensor unit will adapt accordingly. Due to the thermal insulation layer this change, however, occurs only slowly and therefore in a controlled manner. This slow change of the temperature of the sensor unit can be detected reliably already with rather simple temperature measuring devices so that a reliable determination of the concentration of the analyte in the medium is provided continuously.

Another advantage of the device according to the invention is that the at least one temperature measuring device that is used for determining the temperature of the optical sensor unit can be provided in a particularly simple and cost effective manner. In particular no complex temperature measurement device is required which is suitable for detecting short term temperature spikes of the sensor unit.

Furthermore it is advantageous in the device according to the invention that the temperature measuring device can remain within the housing of the device, this means it is arranged at least at a certain distance from the sensor unit since the sensor unit is outside of the housing. In spite of the remote arrangement of the temperature measuring device relative to the sensor unit a reliable statement regarding the temperature of the sensor unit can be made in any case due to the slow variations of the temperature of the sensor unit.

In an advantageous embodiment of the device according to the invention a thickness of the thermal insulation layer is at least 0.5 mm, advantageously at least 1.0 mm, more advantageously at least 1.5 mm. An insulation layer thus configured is particularly well suited to provide a sufficient thermal insulation between the medium and the sensor unit.

Furthermore a device of this type can be particularly advantageous when the material of the insulation layer has a heat conductivity of 0.7 W/mK at the most, advantageously 0.5 W/mK at the most, further advantageously 0.3 W/mK at the most. It is appreciated that using this material is particularly well suited to provide a thermal insulation function.

In another embodiment of the invention the heat transfer coefficient of the insulation layer is 400 W/m$^2$K at the most, advantageously 200 W/m$^2$K at the most, further advantageously 100 W/m$^2$K at the most. Thus, it is irrelevant as a matter of principle whether the described heat transfer coefficient is generated due to a particular thickness of the insulation layer or due to a particularly small heat conductivity of the material used. Ideally the insulation layer has a particular thickness, a comparatively low heat conductivity as well as a comparatively high heat capacity.

Advantageously the insulation layer is made from a hydrophobic material, advantageously from polytetrafluoroethylene (PTFE), in particular sintered polytetrafluoroethylene, or polyethylene (PE), in particular sintered polyethylene (PE). Using a hydrophobic material is advantageous in as far as a precipitation of liquid, in particular water from the gaseous medium hardly occurs on a surface of the insulation layer. A liquid layer of this type which unintentionally precipitates on the surface of the insulation layer poses a risk in particular to block a permeability of the insulation layer for the analyte to be analyzed wherein the permeability from the medium to the optical sensor unit so that the function of the entire device would be impaired. Providing the insulation layer from hydrophobic material prevents these effects. Polyethylene has for example the additional advantage that it has a rather high heat capacity which is in a range of for example approximately 2.1 J/gK.

Advantageously the insulation layer includes a plurality of very small pores, whose maximum pore size is 200 μm, advantageously at the most 100 μm, further advantageously at the most 50 μm. Using this pore size has the particular advantage that a flow of the medium to be analyzed is not possible any more through the thermal insulation layer. Consequently in particular a convective heat exchange between the medium and the optical sensor unit is not possible either. The porosity suffices anyhow in order to facilitate a diffusion of the analyte to be analyzed through the thermal insulation layer and consequently to reach the concentration of the analyte in or at the sensor unit within a very short time period which coincides with the concentration of the analyte directly in the media volume flow. In case for example the concentration of oxygen in an air volume flow shall be analyzed an equilibration of the concentration of the oxygen on both sides of the thermal insulation layer is performed within a few seconds in particular when using the pore size described supra, in particular the equilibration occurs within less than 5 seconds.

In another advantageous embodiment of the device according to the invention the insulation layer is positioned relative to the sensor unit so that insulation layer is in direct contact with the sensor unit. This means that no intentional empty layer is advantageously provided between a bottom side of the insulation layer that is oriented towards the sensor unit and a corresponding surface of the sensor unit. Advantageously the insulation layer covers the entire surface of the sensor unit. Providing the sensor unit and the insulation layer in direct contact with each other has the advantage that no gas layer exists which delays an exchange of the analyte with the sensor unit so that the sensor would react more slowly to changes of the respective condition variable of the analyte.

Independently from the remaining configuration of the device, the device can be particularly advantageous when the optical sensor unit has luminescent properties which are a function of the condition parameter of the analyte in the medium. A sensor unit of this type can be transferred into a luminescent condition by light excitation wherein the luminescent properties of the sensor unit correlate with the concentration at or in the sensor unit. Light emitted by the sensor unit is then detectable by the light receiver wherein a conclusion with respect to the condition parameter of the analyte can be drawn from the properties of the emitted light. Alternatively or in addition to a luminescent sensor unit it is also conceivable to use an absorbing sensor unit which absorbs different amounts of light as a function of the respective condition parameter of the analyte so that monitoring the light that is reflected from the sensor unit due to irradiation also allows a conclusion with respect to the respective condition parameter of the analyte. It is appreciated that additionally or alternatively all additional optical sensor units are conceivable.

In an advantageous embodiment of the device according to the invention the device includes a measuring channel which extends from a wall of the housing and in which the sensor unit and the insulation layer are arranged. The insulation layer is thus sealingly attached at an inner enveloping surface of the measuring channel so that a pass through at least of the analyte is possible between a top side that is oriented away from the sensor unit and a bottom side of the insulation layer that is oriented towards the sensor unit wherein the analyte passes exclusively through the insulation layer. A described measuring channel can include for example a cylindrical or a rectangular cross section wherein the insulation layer or an insulation element forming the insulation layer is advantageously connected circumferentially tight at the inner enveloping surface of the measuring channel. It is appreciated that starting from the housing of the device viewed in a direction towards the medium to be analyzed the insulation layer adjoins the sensor unit so that the latter can thermally insulate from the medium.

The described measuring channel has the particular advantage that an arrangement of the insulation layer is rather simple so that the insulation layer actually thermally insulates relative to the sensor unit. In particular the sensor unit can be flow shielded particularly well from the medium to be analyzed due to a joint effect of a circumferential wall of the measuring channel and the insulation layer or a corresponding insulation element so that an exchange of thermal energy between the medium and the sensor unit is prevented to the largest extent possible.

Advantageously when using the described measuring channel the insulation layer or an insulation element forming the insulation layer is circumferentially glued with the inner enveloping surface of the measuring channel. It is particularly advantageous when the glue has hydrophobic properties so that a precipitation of condensing liquid from an otherwise gaseous medium volume flow is prevented.

As stated supra the thermal insulation of the optical sensor unit from the medium to be analyzed has the effect that the temperature of the sensor unit is subject to much smaller variations than sensor units that are known in the art. Consequently the device according to the invention has the advantage that the respective temperature measuring device that is being used does not have to be in direct contact with the sensor unit in the way in order to be able to detect a change of the temperature of the sensor unit in a sufficiently short time period. Thus, the device according to the invention has the advantage that comparatively simple temperature measuring devices have to be used which can furthermore be arranged at a certain distance from the sensor unit, in particular within the housing of the device. In order to capture a change of the temperature of the sensor unit without time lag it is appreciated that it is particularly advantageous when a heat transmission from the sensor unit to the temperature measuring device can be performed with minimum resistance.

Based on a configuration of the device according to the invention where the temperature measuring device is arranged within the housing and simultaneously the sensor unit is arranged outside of the housing it is particularly advantageous when at least the sensor unit is arranged directly on an outer surface of a wall of the housing. This configuration of the device namely has the advantage that the direct contact between the housing and the sensor unit also facilitates a direct transmission between the sensor unit and the housing. In so far the arrangement according to the invention provides that the temperature of the housing that can be measured on an inside of the wall quickly approaches the temperature of the optical sensor unit. Consequently the arrangement according to the invention facilitates a direct conclusion with respect to the temperature of the sensor unit from measuring the temperature of the housing on an inside of the housing wall.

Thus, it is furthermore particularly advantageous when the housing overall, at least however a divider wall of the housing including the sensor unit have a heat transfer coefficient of at least 50 $W/m^2K$, advantageously at least 75 $W/m^2K$, further advantageously at least 100 $W/m^2K$.

Furthermore it can be particularly advantageous when a ratio between the heat transfer coefficient of the insulation layer and the heat transfer coefficient of the divider wall of the housing is 1:1 at the most, advantageously 0.5:1 at the most, further advantageously 0.3:1 at the most, wherein the divider wall separates an interior space of the housing from a media space where the media is arranged at least from a configuration point of view. This way it is assured that the heat exchange between the temperature measuring device and the sensor unit occurs quicker than between the medium and the sensor unit. Put differently the influence of the temperature of the medium upon the sensor unit is less than the capability to transfer this temperature to the temperature measuring device.

Therefore it is appreciated that an embodiment of the device according to the invention is particularly advantageous where the temperature measuring device arranged in an interior of the housing is in direct contact with the inner surface of the wall of the housing. Advantageously the temperature measuring device is arranged so that a minimum distance of the surface of the sensor unit that is oriented towards the housing and a surface of the temperature measuring device that is oriented towards the housing only corresponds to a thickness of the wall of the housing. Put differently the sensor unit and the temperature measuring device are advantageously arranged at directly opposite locations of the wall of the housing. In this embodiment the path between the travel distance of the thermal energy between the temperature measuring device and the sensor unit is minimized like the reaction time of the temperature measuring device in response to the change of the temperature of the sensor unit.

An integrated temperature sensor can be used as a temperature measuring device in an advantageous embodiment of the invention wherein the temperature sensor is advantageously arranged on a printed circuit board. Temperature sensors of this type are particularly reliable as well as inexpensive. Alternatively or additionally also a temperature measuring device can be used which includes at least one infrared sensor. A temperature measuring device of this type is particularly suited to detect the temperature of the sensor unit or the divider wall contactless wherein the divider wall cooperates with the sensor unit.

BRIEF DESCRIPTION OF THE DRAWINGS

The device according to the invention is subsequently described in more detail based on an embodiment with reference to drawing figures, wherein.

DETAILED DESCRIPTION OF THE INVENTION

Figure 1:
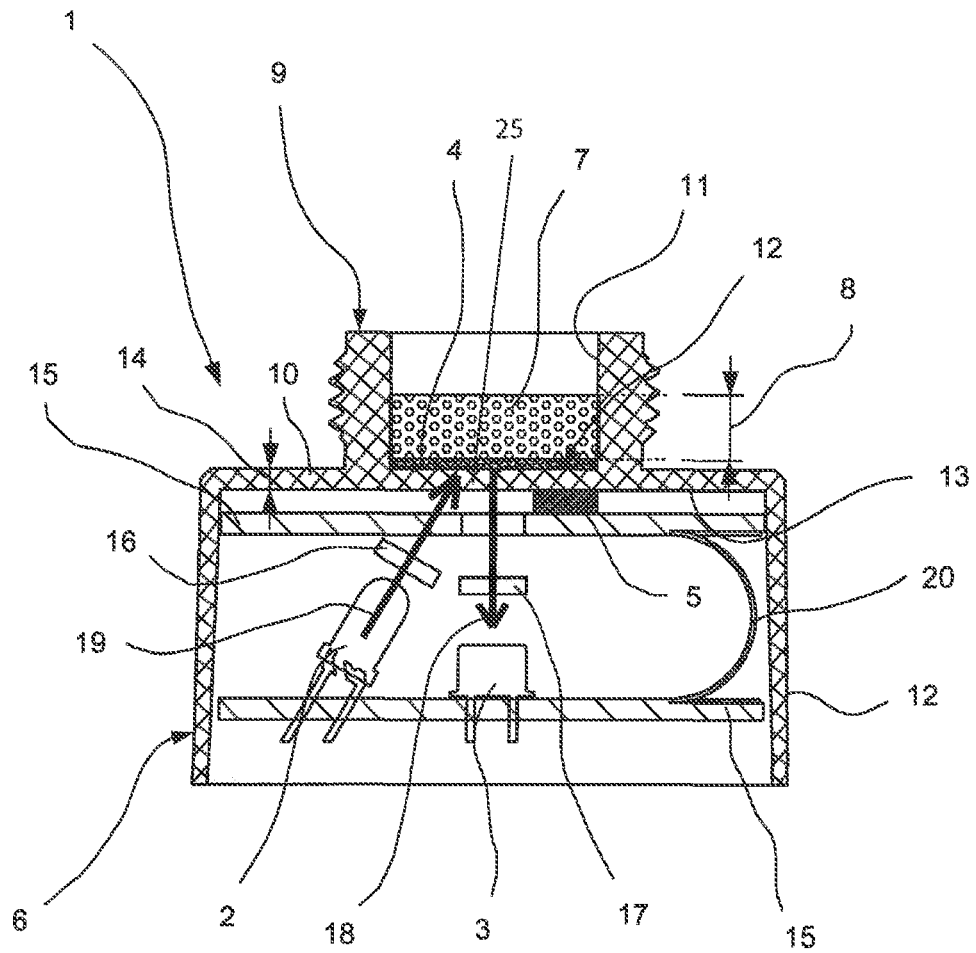
FIG. 1 illustrates a cross section through a device according to the invention.
Figure 2:
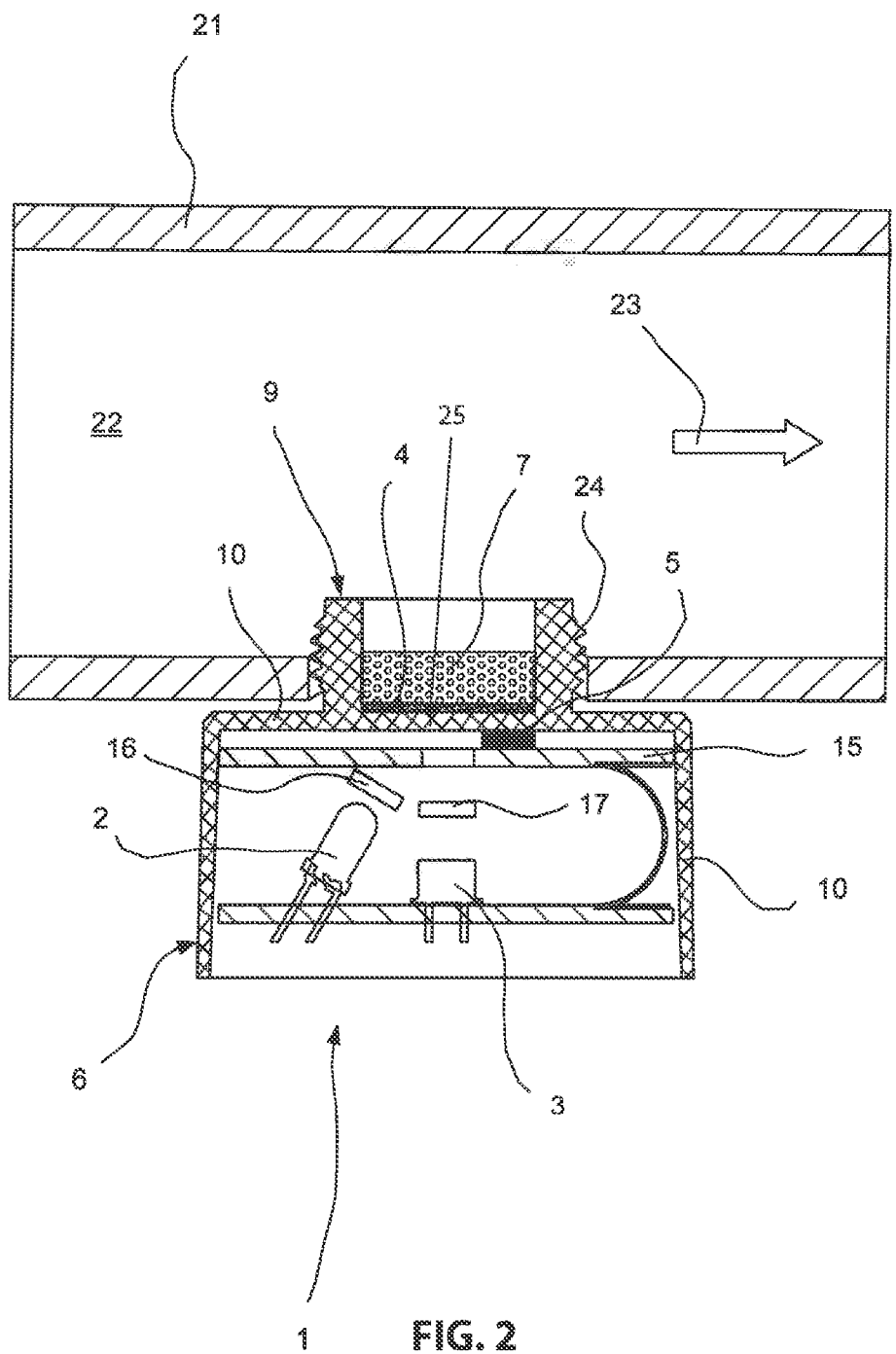
FIG. 2 illustrates a cross section through a media conductor which is provided with the device according to the invention according to FIG. 1.

The embodiment which is illustrated in FIGS. 1 and 2 includes a device 1 according to the invention which includes a light source 2, a light receiver 3 and a sensor unit 4. Furthermore the device 1 includes a temperature measuring device 5 through which the temperature of the sensor unit 4 is detectable. The device 1 is configured so that all electronic components are arranged within the housing 6. The housing 6 is characterized in that it is flow separated from the medium that is to be analyzed, this means an interior space of the housing 6 is shielded from the medium by a wall 10. In particular the interior space is separated by a divider wall 25 from the medium side of the housing 6 wherein the sensor unit 4 is arranged on the medium side of the divider wall 25. The wall 10 of the housing 6, in particular the divider wall 25 are configured transparent herein. The light source 2, the light receiver 3, as well as the temperature measuring device 5 are arranged within the housing 6.

The optical sensor unit 4 is arranged outside of the housing 6 so that a direct exchange of at least individual particles of the analyte is possible between the medium and the sensor unit 4. In the illustrated embodiment the sensor unit 4 is applied directly to an outer surface 12 of the divider wall 25 of the housing 6. The sensor unit 4 is formed by a luminescent color layer which is arranged on an associated carrier. The temperature measuring device 5 is arranged directly on an opposite inner surface 13 of the divider wall 25 so that a distance 14 between the sensor unit 4 and the temperature measuring device 5 is minimal. This has the advantage that a change of the temperature of the sensor unit 4 can be transmitted with minimum delay to the temperature measuring device 5 so that the temperature measured by the temperature measuring device 5 coincides at least essentially with the actual temperature of the sensor unit 4. The divider wall 25 has a heat transfer coefficient of approximately 100 $w/m^2K$.

The temperature measuring device 5 is formed by an integrated temperature sensor which is arranged on a circuit board 15. The circuit board 15 is arranged adjacent to the upper divider wall 25 of the housing 6. The circuit board is furthermore connected with another circuit board 15 by a connecting conductor 20 wherein the other circuit board 15 supports the light source 2 as well as the light receiver 3. The connecting conductor 20 provides an electrical connection between the conductor plates 15.

In the illustrated embodiment the light source 2 is formed by a red LED. Light is emitted towards the optical sensor unit 4 by the light source 2. The light is illustrated in FIG.

1 by the arrow 19. In order to reach the sensor unit 4 the light that is irradiated by the light source 2 has to pass an excitation filter 16 which is configured to only let the wave lengths of the irradiated light pass which are required for exciting the sensor unit 4. In order for the light to impact the sensor unit 4 it is appreciated that the housing 6 has to be transparent at least in the portion cooperating with the sensor unit 4 so that the light emitted by the light source 2 can impact the sensor unit 4. Overall the housing 6 can be formed by a transparent synthetic material.

Due to the excitation of the sensor unit 4 by light emitted by the light source 2 the sensor unit 4 emits light itself, wherein the properties of the light emitted by the sensor unit 4 are a function of the luminescent properties of the sensor unit 4, wherein the luminescence is in turn a function of a concentration of the analyte at or in the sensor unit 4. The light emitted by the sensor unit 4 is then received by the light receiver 3. The light is symbolically illustrated in FIG. 1 by the illustrated arrow 18. An outlet filter 17 is arranged in front of the light receiver 3 wherein the outlet filter 17 lets only wave lengths pass that are emitted by the sensor unit 4 and which are required for analyzing the concentration of the analyte.

The luminescent properties of the sensor unit 4 furthermore depend strongly from the temperature of the sensor unit 4 in addition to the concentration of the respective analyte. Therefore it is only required to monitor the temperature of the sensor unit continuously by the temperature measuring device 5. According to the invention a thermal insulation layer 7 is arranged on the side of the sensor unit 4 that is oriented away from the housing. This has the primarily technical effect that the sensor unit 4 is thermally insulated from the medium to be monitored so that a change of the temperature of the medium at least does not have a direct effect, advantageously no effect upon the temperature of the sensor unit 4. This has the essential advantage that a change of the temperature of the sensor unit 4 over time can be limited to a minimum and thus temperature variations of the sensor unit 4 as a reason for possible measuring errors are eliminated. Furthermore there is a particular advantage that the employed temperature measuring device 5 can be configured comparatively simple since in particular sudden changes of the temperature of the sensor unit 4 by considerable amounts are not to be expected. In particular it is not necessary compared to the prior art to bring the temperature measuring device 5 in direct contact with the sensor unit 4 and thus to run it out of the housing 6 of the device 1. Instead the temperature measuring device 5 can remain within the housing 6.

The thermal insulation layer 7 has a thickness 8 of approximately 2 mm. By comparison the carrier of the optical sensor unit 4 has a thickness of approximately 0.1 mm. The luminescent color layer of the sensor unit 4 as such only has a thickness of approximately 0.01 mm. The heat transfer coefficient of the insulation layer 7 is 30 w/m$^2$K. Thus, the ratio of the heat transfer coefficient of the insulation layer 7 and the housing 6 or the divider wall 25 is 0.3/1.

In the illustrated embodiment the thermal insulation layer 7 is formed from sintered polytetrafluorethylene. Accordingly the insulation layer 7 includes a plurality of micro pores which facilitate in particular a diffusion of the analyte from a top side of the insulation layer 7 oriented away from the housing 6 to a bottom side of the insulation layer 7 oriented towards the housing 6. The pores of the insulation layer 7 thus have a size of 30 μm. Furthermore the insulation layer 7 is arranged at the device 1 so that a direct contact between the medium to be examined and the sensor unit 4 is prevented. Thus, the device 1 includes a measuring channel 9 which extends from the housing 6. The sensor unit 4 is arranged at a lower end of the measuring channel 9 that is oriented towards the housing 6 and the insulation layer 7 is accordingly arranged there above. The sensor unit 7 is positioned so that its bottom side is in direct contact with a surface of the sensor unit 4 that is oriented away from the housing 6. Put differently there is no empty layer for example an air layer between the surfaces of the insulation layer 7 that are oriented towards each other and the sensor unit 4.

Using polytetrafluorethylene is particularly advantageous since it has hydrophobic properties which prevent a formation of a liquid film on a top side of the insulation layer 7. This assures that the pores of the insulation layer 7 through which the respective analyte has to migrate to the sensor unit 4 are not sealed by a precipitating liquid. In addition to the insulation layer 7 furthermore also the glue is hydrophobic wherein the insulation layer is connected in the illustrated embodiment with the inner enveloping surface 11 of the measuring channel 9.

FIG. 2 illustrates a potential installation of a device 1 according to the invention. Thus, the measuring channel 9 includes an exterior thread 24 at an outer enveloping surface wherein the interior thread cooperates with a complementary inner thread of a media conductor 21. In the media conductor 21 a medium 22 that is to be examined, for example breathing air, is run in a flow direction 23. Thus, the medium 22 flows directly along the device 1, wherein a direct exchange of a respective analyte is possible between the medium 22 and the sensor unit 4 through the insulation layer 7. For example is conceivable that the concentration of oxygen in the medium 22 shall be analyzed. It is evident from the illustration that the medium 22 is at least thermally decoupled from the sensor unit 4 by the insulation layer 7 so that temperature variations of the medium 22 do not have any direct effect upon the temperature of the sensor unit 4. By the same token the porosity of the insulation layer 7 facilitates particularly quick diffusion of the individual components of the analyte to be analyzed through the insulation layer 7 so that the concentration of the respective analyte in or at the sensor unit 4 has adapted to the concentration of the analyte in the medium 22 in particular within less than 2 seconds. Thus, the insulation layer 7 according to the invention does not impede a particularly short response time of the sensor unit 4.

REFERENCE NUMERALS AND DESIGNATIONS 1 device
2 light source
3 light receiver
4 sensor unit
5 temperature measuring device
6 housing
7 insulation layer
8 thickness
9 measuring channel
10 wall
11 inner enveloping surface
12 outer surface
13 inner surface
14 distance
15 printed circuit board
16 excitation filter
17 exit filter 18 arrow
19 arrow
20 connecting conductor
21 media conductor
22 medium
23 flow direction
24 external thread
25 divider wall

What is claimed is:

1. A device for determining at least one condition parameter relating to a concentration or a partial pressure of an analyte in a gaseous medium, the device comprising:
   at least one light source configured to emit light;
   at least one light receiver configured to detect the light;
   at least one optical sensor unit; and
   at least one temperature measuring device configured to measure a temperature of the at least one optical sensor unit at least indirectly,
   wherein at least the at least one light source, the at least one light receiver and the at least one temperature measuring device are arranged within a housing and at least the at least one optical sensor unit is arranged outside of the housing,
   wherein at least one optical property of the at least one optical sensor unit is a function of the at least one condition parameter of the analyte,
   wherein light rays emitted by the at least one optical sensor unit due to the at least one optical sensor unit being irradiated by the at least one light source are detectable by the at least one light receiver,
   wherein data derived from the light rays detected by the at least one light receiver facilitate a conclusion regarding the at least one condition parameter of the analyte in the medium,
   wherein at least one thermal insulation layer which is arranged on a side of the at least one optical sensor unit that is oriented away from the housing is configured to insulate the at least one optical sensor unit from the medium at least thermally,
   wherein a ratio between a heat transfer coefficient of the insulation layer and a heat transfer coefficient of a divider wall of the housing is 1:1 at the most, and
   wherein the divider wall separates an inner space of the housing at least structurally from a media space in which the medium is arranged.

2. The device according to claim 1, wherein a thickness of the at least one thermal insulation layer is at least 0.5 mm.

3. The device according to claim 1, wherein a material from which the at least one thermal insulation layer is formed has a heat conductivity of 0.7 W/mK at the most.

4. The device according to claim 1, wherein a heat transfer coefficient of the at least one thermal insulation layer is 400 $W/m^2K$ at the most.

5. The device according to claim 1, wherein the at least one thermal insulation layer is formed from a hydrophobic material or from polytetrafluorethylene or from sintered polytetrafluorethylene.

6. The device according to claim 1, wherein the at least one thermal insulation layer has pores with a size of 200 μm at the most.

7. The device according to claim 1,
   wherein the at least one thermal insulation layer is in direct contact with the at least one optical sensor unit, and
   wherein the at least one thermal insulation layer covers an entire surface of the at least one optical sensor unit that is oriented away from the housing.

8. The device according to claim 1,
   wherein the at least one optical sensor unit has luminescent properties which are a function of the at least one condition parameter of the analyte in the medium,
   wherein the at least one optical sensor unit is transferable into a luminescent condition,
   wherein luminescent properties of the at least one optical sensor unit correlate with the concentration of the analyte at or in the at least one optical sensor unit, and
   wherein the light rays that are emitted by the at least one optical sensor unit due to excitation is detectable by the at least one light receiver so that captured data facilitates a conclusion regarding the at least one condition parameter of the analyte in the medium.

9. The device according to claim 1, further comprising:
   a measuring channel that extends from a wall of the housing and in which the at least one optical sensor unit and the at least one thermal insulation layer are arranged,
   wherein the at least one thermal insulation layer is connected in a sealing manner to an inner enveloping surface of the measuring channel so that a passage at least of the analyte is facilitated exclusively through the at least one thermal insulation layer between a side of at least one thermal insulation layer that is oriented away from the at least one optical sensor unit and a side of the at least one thermal insulation layer that is oriented towards the at least one optical sensor unit.

10. The device according to claim 1, wherein the at least one optical sensor unit is directly arranged on an outer surface of a wall of the housing.

11. The device according to claim 1, wherein the at least one temperature measuring device is formed by an integrated temperature sensor that is arranged at a printed circuit board.

12. The device according to claim 1, wherein the insulation layer has a heat capacity of at least 0.3 J/gK.

13. A device for determining at least one condition parameter relating to a concentration or a partial pressure of an analyte in a gaseous medium, the device comprising:
    at least one light source configured to emit light;
    at least one light receiver configured to detect the light;
    at least one optical sensor unit; and
    at least one temperature measuring device configured to measure a temperature of the at least one optical sensor unit at least indirectly,
    wherein at least the at least one light source, the at least one light receiver and the at least one temperature measuring device are arranged within a housing and at least the at least one optical sensor unit is arranged outside of the housing,
    wherein at least one optical property of the at least one optical sensor unit is a function of the at least one condition parameter of the analyte,
    wherein light rays emitted by the at least one optical sensor unit due to the at least one optical sensor unit being irradiated by the at least one light source are detectable by the at least one light receiver,
    wherein data derived from the light rays detected by the at least one light receiver facilitate a conclusion regarding the at least one condition parameter of the analyte in the medium,
    wherein at least one thermal insulation layer which is arranged on a side of the at least one optical sensor unit that is oriented away from the housing is configured to insulate the at least one optical sensor unit from the medium at least thermally, a measuring channel that extends from a wall of the housing and in which the at least one optical sensor unit and the at least one thermal insulation layer are arranged, wherein the at least one thermal insulation layer is connected in a sealing manner to an inner enveloping surface of the measuring channel so that a passage at least of the analyte is facilitated exclusively through the at least one thermal insulation layer between a side of at least one thermal insulation layer that is oriented away from the at least one optical sensor unit and a side of the at least one thermal insulation layer that is oriented towards the at least one optical sensor unit, wherein the at least one thermal insulation layer is circumferentially glued to the inner enveloping surface of the measuring channel by a glue, and wherein the glue has hydrophobic properties.

14. A device for determining at least one condition parameter relating to a concentration or a partial pressure of an analyte in a gaseous medium, the device comprising:

at least one light source configured to emit light;
at least one light receiver configured to detect the light;
at least one optical sensor unit; and
at least one temperature measuring device configured to measure a temperature of the at least one optical sensor unit at least indirectly, wherein at least the at least one light source, the at least one light receiver and the at least one temperature measuring device are arranged within a housing and at least the at least one optical sensor unit is arranged outside of the housing, wherein at least one optical property of the at least one optical sensor unit is a function of the at least one condition parameter of the analyte, wherein light rays emitted by the at least one optical sensor unit due to the at least one optical sensor unit being irradiated by the at least one light source are detectable by the at least one light receiver, wherein data derived from the light rays detected by the at least one light receiver facilitate a conclusion regarding the at least one condition parameter of the analyte in the medium, wherein at least one thermal insulation layer which is arranged on a side of the at least one optical sensor unit that is oriented away from the housing is configured to insulate the at least one optical sensor unit from the medium at least thermally, wherein the at least one temperature measuring device is in direct contact with an inner surface of an outer wall of the housing, and wherein the at least one temperature measuring device is arranged so that a minimum distance between a surface of the at least one optical sensor unit that is oriented towards the housing and the at least one temperature measuring device corresponds to a thickness of a wall of the housing.

* * * * *